(12) United States Patent
Ikemoto

(10) Patent No.: US 9,732,079 B2
(45) Date of Patent: Aug. 15, 2017

(54) YELLOW REDUCED PYRROLOQUINOLINE QUINONE CRYSTAL AND METHOD OF PRODUCING THE SAME, AND FOOD, PHARMACEUTICAL, GEL, COMPOSITION AND METHOD OF PRODUCING COMPOSITION

(71) Applicant: Mitsubishi Gas Chemical Company, Inc., Chiyoda-ku (JP)

(72) Inventor: Kazuto Ikemoto, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 14/786,846

(22) PCT Filed: Apr. 23, 2014

(86) PCT No.: PCT/JP2014/061412
§ 371 (c)(1),
(2) Date: Oct. 23, 2015

(87) PCT Pub. No.: WO2014/175327
PCT Pub. Date: Oct. 30, 2014

(65) Prior Publication Data
US 2016/0075700 A1    Mar. 17, 2016

(30) Foreign Application Priority Data
Apr. 26, 2013   (JP) ................ 2013-093264

(51) Int. Cl.
| | | |
|---|---|---|
| A61K 31/4745 | (2006.01) | |
| C07D 471/04 | (2006.01) | |
| A61K 47/10 | (2017.01) | |
| A61K 47/40 | (2006.01) | |
| A61K 9/10 | (2006.01) | |
| A61K 9/14 | (2006.01) | |
| C08B 37/16 | (2006.01) | |
| C08L 5/16 | (2006.01) | |
| A61K 8/49 | (2006.01) | |
| A61Q 19/00 | (2006.01) | |
| A23L 33/10 | (2016.01) | |

(52) U.S. Cl.
CPC ............ *C07D 471/04* (2013.01); *A23L 33/10* (2016.08); *A61K 8/494* (2013.01); *A61K 9/10* (2013.01); *A61K 9/146* (2013.01); *A61K 31/4745* (2013.01); *A61K 47/10* (2013.01); *A61K 47/40* (2013.01); *A61Q 19/00* (2013.01); *C08B 37/0015* (2013.01); *C08L 5/16* (2013.01); *A23V 2002/00* (2013.01)

(58) Field of Classification Search
CPC ..................................................... C07D 471/04
USPC .......................................................... 546/79
See application file for complete search history.

(56) References Cited

U.S. PATENT DOCUMENTS

| | | | | | |
|---|---|---|---|---|---|
| 5,460,819 | A | * | 10/1995 | Gallop | ................... A61K 31/47 514/292 |
| 7,144,709 | B2 | * | 12/2006 | Ouyang | ................... C12Q 1/26 422/534 |
| 2012/0323009 | A1 | | 12/2012 | Ikemoto et al. | |
| 2013/0203869 | A1 | | 8/2013 | Mikekado et al. | |

FOREIGN PATENT DOCUMENTS

| | | |
|---|---|---|
| CN | 102770432 A | 11/2012 |
| JP | 2012-180319 A | 9/2012 |
| WO | WO 2011/102367 A | 8/2011 |
| WO | WO 2012/020767 A | 2/2012 |
| WO | WO 2013/073642 A1 | 5/2013 |

OTHER PUBLICATIONS

International Search Report issued Aug. 5, 2014, in PCT/JP2014/061412 filed Apr. 23, 2014.
Itoh, S. et al., "Reaction of reduced PQQ ($PQQH_2$) and Molecular Oxygen", Bulletin of the Chemical Society of Japan, (Jun. 1986), vol. 59, No. 6, p. 1911-14.
Ouchi, A. et al., "Kinetic Study of the Antioxidant Activity of Pyrroloquinolinequinol (PQQH2, a Reduced Form of Pyrroloquinolinequinone) in Micellar Solution", Journal of Agricultural and Food Chemistry, vol. 57, No. 2, (2009), pp. 450-456.
Duine, J.A. et al., "Characterization of the Second Prosthetic Group in Methanol Dehydrogenase from Hyphomicrobium X", Eur. J. Biochem., vol. 118, (1981), pp. 395-399.
Duine, J.A. et al., "Structure and Activity of the Prosthetic Group of Methanol Dehydrogenase", Eur. J. Biochem., vol. 108, (1980), pp. 187-192.

* cited by examiner

*Primary Examiner* — Rita Desai
(74) *Attorney, Agent, or Firm* — Oblon, McClelland, Maier & Neustadt, L.L.P.

(57) ABSTRACT

A yellow reduced pyrroloquinoline quinone crystal having a solubility in water of 0.040 to 0.20 (mg/mL).

18 Claims, 9 Drawing Sheets

YELLOW REDUCED PYRROLOQUINOLINE QUINONE CRYSTAL AND METHOD OF PRODUCING THE SAME, AND FOOD, PHARMACEUTICAL, GEL, COMPOSITION AND METHOD OF PRODUCING COMPOSITION

TECHNICAL FIELD

The present invention relates to a yellow reduced pyrroloquinoline quinone crystal and a method of producing the same, and a food, a pharmaceutical, a gel, a composition and a method of producing a composition.

BACKGROUND ART

Reduced pyrroloquinoline quinone (hereinafter also referred to as "reduced PQQ") is a substance obtained by reducing the quinone moiety of oxidized pyrroloquinoline quinone (hereinafter also referred to as "oxidized PQQ").

It has been reported that the reduced pyrroloquinoline quinone has much higher antioxidant activity than the conventional oxidized PQQ (Non Patent Literature 1). It is presumed that the oxidized PQQ is reduced in vivo into reduced PQQ, which seems to act as active species causing proliferation of cells or a reduction in blood sugar level. For this reason, the reduced PQQ is more effective than the oxidized PQQ, and has been receiving attention as a useful component in applications to, for example, nutritional functional foods, foods for specified health uses, nutritious supplements, nutrients, beverages, feedstuffs, animal drugs, cosmetics, pharmaceuticals, therapeutic drugs, and preventive drugs.

It has been reported that the reduced PQQ is obtained by reduction of oxidized PQQ with a typical reducing agent such as sodium borohydride or sodium dithionite, reduction of oxidized PQQ with hydrogen in the presence of a platinum catalyst, or reduction of oxidized PQQ with glutathione (for example, see Non Patent Literatures 1, 2, 3, and 4).

Patent Literature 1 proposes a method of reducing PQQ with ascorbic acid.

CITATION LIST

Patent Literature

Patent Literature 1: WO 2011/102387

Non Patent Literature

Non Patent Literature 1: J. Agric. Food Chem. 2009, 57, 450-456
Non Patent Literature 2: Bull. Chem. Soc. Jpn, 59, 1911-1914 (1986)
Non Patent Literature 3: Eur. J. Biochem., 118, 395-399 (1981)
Non Patent Literature 4: Eur. J. Biochem., 108, 187-192 (1980)

SUMMARY OF INVENTION

Technical Problem

In the applications to foods, pharmaceuticals and the like, it is desired that the reduced PQQ have high safety, be prepared by a simple process at low cost, be homogeneously dispersed in liquids, and have a light color (be unlikely to color substances to be added).

Unfortunately, the typical reducing agents described in Non Patent Literature 1 highly probably have toxicity to a living body, and requires a step of removing the toxicity. The reducing agent described in Non Patent Literature 2 uses hydrogen readily leaked and exploded, and requires a special facility. A problem of Non Patent Literatures 3 and 4 is that glutathione is expensive.

A problem of the method described in Patent Literature 1 is that black reduced PQQ crystals are readily obtained and are not difficult to use in foods, cosmetics and the like. Moreover, the conventional black reduced PQQ crystals are soluble in aprotic solvents such as dimethyl sulfoxide whereas these crystals have very low solubility in water and alcohol. Accordingly, these crystals are difficult to use in the form of liquid in the applications to foods, pharmaceuticals and the like.

Furthermore, in the conventional method of producing reduced PQQ, the reduced PQQ is recrystallized with dimethyl sulfoxide and acetonitrile, is discharged from a column using a mixed solvent of methanol and water, and the resulting solution is dried to obtain reduced PQQ. In this method, however, the organic solvent may remain in the reduced PQQ. The reduced PQQ having a residual organic solvent cannot be used in foods without any treatment. Use of such an organic solvent requires a facility for combustible materials in the production, leading to an increase in production cost. Use of the column requires an expensive facility and a large amount of a solution for extraction, which are not preferable.

The present invention has been made in consideration of such problems. An object of the present invention is to provide a reduced pyrroloquinoline quinone crystal having excellent solubility and a light color such as yellow color and a simple method of producing the reduced pyrroloquinoline quinone crystal, and a food, a pharmaceutical, a gel, and a composition and a method of producing a composition.

Solution to Problem

The present inventors have conducted extensive research to solve the problems above, and as a result, have found that a predetermined reduced pyrroloquinoline quinone crystal can solve these problems, and have achieved the present invention.

Namely, the present invention is as follows:

[1] A yellow reduced pyrroloquinoline quinone crystal having a solubility in water of 0.040 to 0.20 (mg/mL).

[2] The yellow reduced pyrroloquinoline quinone crystal according to [1], wherein the yellow reduced pyrroloquinoline quinone crystal has 2θ peaks at 6.85±0.4°, 10.49±0.4°, 11.02±0.4°, 16.18±0.4°, 23.57±0.4°, and 25.36±0.4° in powder X-ray diffraction using Cu-Kα.

[3] The yellow reduced pyrroloquinoline quinone crystal according to [1] or [2], wherein the yellow reduced pyrroloquinoline quinone crystal comprises a reduced pyrroloquinoline quinone in a free form.

[4] A food comprising the yellow reduced pyrroloquinoline quinone crystal according to any one of [1] to [3].

[5] A pharmaceutical comprising the yellow reduced pyrroloquinoline quinone crystal according to any one of [1] to [3].

[6] A gel comprising the yellow reduced pyrroloquinoline quinone crystal according to any one of [1] to [3] and ethanol.

[7] A food comprising the gel according to [6].

[8] A composition comprising the yellow reduced pyrroloquinoline quinone crystal according to any one of [1] to [3] and cyclodextrin.

[9] The composition according to [8], wherein the cyclodextrin comprises γ-cyclodextrin.

[10] The composition according to [8] or [9], wherein a content of the cyclodextrin is 1 to 2000 parts by mass based on 1 part by mass of the yellow reduced pyrroloquinoline quinone crystal.

[11] The composition according to any one of [8] to [10], further comprising water.

[12] A method of producing a composition, comprising a step of removing ethanol and/or water from a solution containing the yellow reduced pyrroloquinoline quinone crystal according to any one of [1] to [3], cyclodextrin, the ethanol and/or the water.

[13] A method of producing a yellow reduced pyrroloquinoline quinone crystal, comprising a step of stirring a mixed solution containing pyrroloquinoline quinone and/or a salt of the pyrroloquinoline quinone and a reducing agent at a temperature of less than 25° C. for 10 hours or more.

[14] The method of producing the yellow reduced pyrroloquinoline quinone crystal according to [13], wherein the reducing agent comprises ascorbic acid.

[15] The method of producing the yellow reduced pyrroloquinoline quinone crystal according to [13] or [14], wherein the mixed solution has a pH of 1.5 to 3.5.

[16] The method of producing the yellow reduced pyrroloquinoline quinone crystal according to any one of [13] to [15], wherein a total content of the pyrroloquinoline quinone and the salt of the pyrroloquinoline quinone in the mixed solution is 0.0010 to 30 g/L.

[17] The method of producing the yellow reduced pyrroloquinoline quinone crystal according to any one of [13] to [16], wherein a content of the reducing agent in the mixed solution is 0.10 to 500 g/L.

Advantageous Effects of Invention

The present invention can provide a reduced pyrroloquinoline quinone crystal having excellent solubility and a light color such as yellow color and a simple method of producing the reduced pyrroloquinoline quinone crystal, and a food, a pharmaceutical, a gel, and a composition and a method of producing a composition.

DESCRIPTION OF EMBODIMENT

Figure 1:
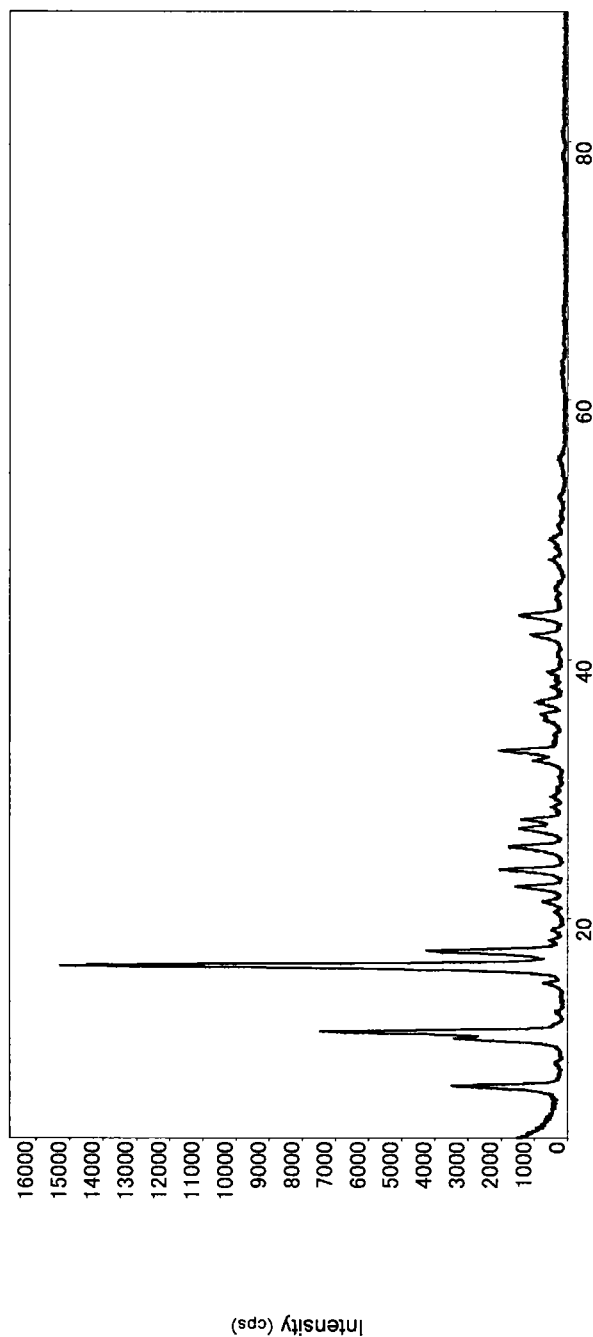
FIG. 1 shows a drawing showing the result of powder X-ray diffraction of a yellow ocher reduced pyrroloquinoline quinone crystal in Example 1.

The embodiment for implementing the present invention (hereinafter referred to as "the present embodiment") will now be described in detail, but the present invention is not limited to this, and can be modified in various ways within the scope of the gist.

[Yellow Reduced Pyrroloquinoline Quinone Crystal]

The reduced pyrroloquinoline quinone crystal according to the present embodiment is a yellow crystal having a solubility in water of 0.040 to 0.20 (mg/mL). The reduced pyrroloquinoline quinone is represented by Formula (1):

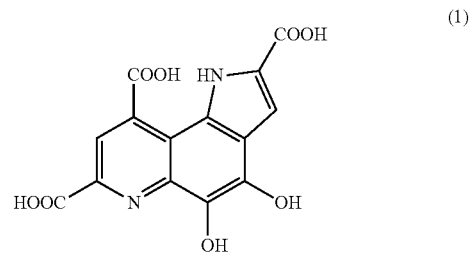 [SMILES: O=C(O)c1cc(C(=O)O)c2c(n1)c(O)c(O)c1cc(C(=O)O)[nH]c12]

The yellow reduced pyrroloquinoline quinone crystal has a solubility in water of 0.040 to 0.20 (mg/mL), preferably 0.060 to 0.18 (mg/mL), more preferably 0.080 to 0.16 (mg/mL). At a solubility in water within this range, the solution prepared by mixing the crystals into a liquid is readily kept homogeneous, and thus is more readily used in applications such as foods and pharmaceuticals.

The yellow reduced pyrroloquinoline quinone crystal has a solubility in ethanol of 1.8 to 12.5 (mg/mL), preferably 2.0 to 10 (mg/mL), more preferably 2.5 to 9.0 (mg/mL). At a solubility in ethanol within this range, the solution is more readily used in the applications to foods, pharmaceuticals and the like.

It seems that one non-limiting reason why the yellow reduced pyrroloquinoline quinone crystal according to the present embodiment has such a high solubility in water is that when the crystal dissolves in water, a process is present where water molecules gather around the crystal molecules to cause hydration, and the crystal has an arrangement readily allowing hydration of a hydrophilic group.

The yellow reduced pyrroloquinoline quinone crystal has high enough dispersibility to very readily form a solution having fluidity. Here, the term "high dispersibility" indicates that in a concentration exceeding the solubility of a solvent, the crystals not dissolved in the solvent are homogeneously dispersed in the solvent.

The reduced pyrroloquinoline quinone crystal according to the present embodiment is a yellow crystal having a hue of preferably 50° to 70°. The method of measuring the hue is not particularly limited, and the hue can be measured using a commercially available spectrocolorimeter.

The yellow reduced pyrroloquinoline quinone crystal has 2θ peaks at 6.85±0.4°, 10.49±0.4°, 11.02±0.4°, 16.18±0.4°, 23.57±0.4°, and 25.36±0.4° in the powder X-ray diffraction using Cu-Kα. The specific measurement conditions on the powder X-ray diffraction using Cu-Kα are as described in Examples.

Besides, the yellow reduced pyrroloquinoline quinone crystal can be observed with a typical powder X-ray diffraction apparatus equipped with a monochromator. It should be noted that the shapes of the crystals specified in the present invention have errors of measurement. Therefore, the crystals may be rationally identical with respect to the angle of the peak.

The yellow reduced pyrroloquinoline quinone crystal preferably contains a free form of a pyrroloquinoline quinone molecule having no ionic bond of a metal atom of an alkali metal or the like to a carboxylic acid group (hereinafter also referred to as a "free form"). The content of a metal atom in the yellow reduced pyrroloquinoline quinone crystal is preferably 0 to 200 mol %, more preferably 0 to 150 mol %, still more preferably 0 to 100 mol % based on 100 mol % of pyrroloquinoline quinone. A content of the metal atom within this range can more stably maintain the crystal structure, and tends to more significantly prevent change in color of the crystal to red or black and a reduction in the solubility in water. The content of the metal atom can be measured by the method described in Examples.

The content of water in the yellow reduced pyrroloquinoline quinone crystal is preferably 0 to 50% by mass, more preferably 0 to 30% by mass, still more preferably 5 to 15% by mass based on 100% by mass of the yellow reduced pyrroloquinoline quinone crystal. A content of water within this range can more stably maintain the crystal structure, and tends to more significantly prevent change in color of the crystal to red or black and a reduction in the solubility in water. The content of water can be measured with a Karl-Fischer infrared moisture meter.

[Method of Producing Yellow Reduced Pyrroloquinoline Quinone Crystal]

The method of producing the yellow reduced pyrroloquinoline quinone crystal according to the present embodiment comprises a step of stirring a mixed solution containing pyrroloquinoline quinone and/or a salt of the pyrroloquinoline quinone and a reducing agent at a temperature of less than 25° C. for 10 hours or more. Such a method can attain yellow crystals without the conventional recrystallization step, and can more significantly simplify the refining step to attain a simple method of producing the yellow reduced pyrroloquinoline quinone crystal.

[Pyrroloquinoline Quinone and Salts Thereof]

Examples of the pyrroloquinoline quinone and/or the salt of the pyrroloquinoline quinone include, but are not particularly limited to, pyrroloquinoline quinone (in the free form) represented by Formula (2) and salts thereof:

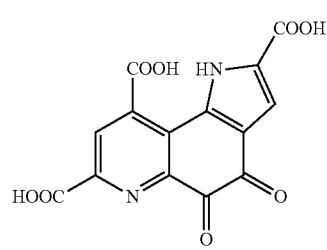

(2)

Examples of the "salt of the pyrroloquinoline quinone" include alkali metal salts, alkaline earth metal salts, and ammonium salts of the pyrroloquinoline quinone. Among these salts, preferred are alkali metal salts from the viewpoint of availability. Examples of the alkali metal salts include, but are not particularly limited to, disodium salts and dipotassium salts. The pyrroloquinoline quinone or the salts thereof used in the present invention can be obtained in the form of a commercially available product, or can be produced by any known method.

The pyrroloquinoline quinone or the salts thereof can be used in the form of a solution of the pyrroloquinoline quinone or the salts thereof. Any solvent which progresses a reaction, such as water, alcohol, and dimethyl sulfoxide can be used without particular limitation. Preferred is water from the viewpoint of safety in the applications to foods, pharmaceuticals and the like.

The total content of the pyrroloquinoline quinone and the salts thereof in the mixed solution is preferably 0.0010 to 30 g/L, more preferably 0.01 to 15 g/L, still more preferably 0.1 to 5 g/L. A total content of the pyrroloquinoline quinone and the salts thereof of 0.0010 g/L or more tends to enhance the productivity more significantly. A total content of the pyrroloquinoline quinone and the salts thereof of 30 g/L or less tends to enhance the workability more significantly.

[Reducing Agent]

Examples of the reducing agent include, but are not particularly limited to, ascorbic acids. Among these ascorbic acids, preferred is L-ascorbic acid. Use of ascorbic acid tends to provide an enhanced cost competitiveness. The ascorbic acid can be used in the form of a commercially available product or can be produced by any known method for use. The reducing agent can be used in the form of a dissolution in water or alcohol. Among these forms, preferred is the form of an aqueous solution for use.

The content of the reducing agent in the mixed solution is 0.10 to 500 g/L, more preferably 0.50 to 300 g/L. A content of the reducing agent of 0.10 g/L or more tends to enhance the reaction rate more significantly. A content of the reducing agent of 500 g/L or less tends to enhance the uniformity of the reaction solution more significantly.

[Stirring Temperature]

The stirring temperature is less than 25° C., preferably 0° C. to less than 25° C., more preferably 0° C. to 20° C. or less. A stirring temperature of less than 25° C. enhances the crystallinity of the resulting crystals having a yellow color and enhances the solubility of the crystals. The yellow crystals are relatively unlikely to color substances to be mixed, and thus applications thereof are unlikely to be limited. A stirring temperature of 0° C. or more tends to enhance production efficiency of the crystal more significantly. If the same reducing agent is used at different reaction temperatures, the resulting pyrroloquinones may have different crystal structures. In particular, if the stirring temperature is 25° C. or more, the resulting crystal has reduced crystallinity and the color closer to black. The crystal having a color closer to black may be limited in applications.

[Stirring Time]

The stirring time is 10 hours or more, preferably 10 hours or more and within one week, more preferably 15 hours or more and within five days. A stirring time of 10 hours or more enhances the crystallinity of the resulting crystal more significantly. A stirring time of within one week enhances the production efficiency of the crystal more significantly.

[Stirring Method]

The stirring method is not particularly limited and can be performed using, for example, a shaker incubator, a magnetic stirrer or the like. With stirring, the crystallization rate and the crystallinity of the resulting crystal are enhanced and the crystal has a yellow color and an enhanced solubility of the crystal. The yellow crystals are relatively unlikely to color substances to be mixed, and thus applications thereof are unlikely to be limited. Without stirring, the crystallinity of the resulting crystal is unlikely to be enhanced, and black crystals are obtained.

[pH]

The mixed solution has a pH of preferably 1.5 to 3.5, more preferably 1.7 to 3.2. A mixed solution having a pH of 1.5 or more tends to prevent generation of black crystals and efficiently attain yellow crystals. A mixed solution having a pH of 3.5 or less tends to enhance reduction stability more significantly. The pH of the mixed solution should not be always within this range through the entire stirring step. Preferably, the pH of the mixed solution is at least within this range when the pyrroloquinoline quinone and/or the salt of the pyrroloquinoline quinone, and the reducing agent are all mixed to prepare a mixed solution. The pH of the mixed solution may be adjusted at any point of time of the initial, middle, and final stirring stages.

The method of preparing the mixed solution is not particularly limited. Preferably, for example, a reducing agent solution containing a reducing agent and a pyrroloquinoline quinone solution containing pyrroloquinoline quinone are made available, and the pyrroloquinoline quinone solution is added to the reducing agent solution. The addition of the pyrroloquinoline quinone solution to the reducing agent solution tends to more significantly reduce the viscosity of the resulting mixed solution and more significantly enhance the stirring efficiency.

Through the stirring step, the yellow reduced pyrroloquinoline quinone crystals are precipitated from the mixed solution. The production method according to the present embodiment can attain yellow reduced pyrroloquinoline quinone crystals without the conventional recrystallization step, simplifying the refining step more significantly.

The yellow reduced pyrroloquinoline quinone crystals obtained through the stirring step can be separated through filtration or centrifugation. The separated yellow reduced pyrroloquinoline quinone crystals are preferably washed with water, an organic solvent or the like, and are then dried under reduced pressure or the like. The drying temperature is preferably 120° C. or less, more preferably 70° C. or less from the viewpoint of prevention of change in color of the crystals. The lower limit of the drying temperature is not particularly limited, and is preferably room temperature or more.

[Composition]

The composition according to the present embodiment comprises the yellow reduced pyrroloquinoline quinone crystal and cyclodextrin. In the composition, a clathrate cyclodextrin traps the yellow reduced pyrroloquinoline quinone crystal to likely provide an enhanced solubility of the yellow reduced pyrroloquinoline quinone crystal.

The composition according to the present embodiment may be in the form of powder or a solution containing water or ethanol.

(Cyclodextrin)

Examples of the cyclodextrins include, but are not particularly limited to, α-cyclodextrin, β-cyclodextrin, and γ-cyclodextrin. Among these compounds, preferred is γ-cyclodextrin. Use of such the cyclodextrin tends to enhance the solubility of the yellow reduced pyrroloquinoline quinone crystal more significantly.

The content of the cyclodextrin is preferably 1 to 2000 parts by mass, more preferably 1 to 1000 parts by mass, still more preferably 1 to 500 parts by mass, further still more preferably 1 to 50 parts by mass, still more preferably 5 to 500 parts by mass based on 1 part by mass of the yellow reduced pyrroloquinoline quinone crystal. A content of the cyclodextrin of 1 part by mass or more tends to enhance the solubility of the yellow reduced pyrroloquinoline quinone crystal more significantly. A content of the cyclodextrin of 2000 parts by mass or less tends to enhance the solubility more significantly.

(Water)

The composition may further contain water. The content of water is preferably 0 to 50 parts by mass, more preferably 0 to 30 parts by mass, still more preferably 2 to 20 parts by mass based on 100 parts by mass of the yellow reduced pyrroloquinoline quinone crystal. A content of water of 2 parts by mass or more tends to enhance the crystallinity more significantly. A content of water of 50 parts by mass or less tends to enhance stability more significantly.

(Ethanol)

The composition may further contain ethanol. The content of ethanol is preferably 0 to 200 parts by mass, more preferably 0 to 100 parts by mass, still more preferably 5 to 50 parts by mass based on 100 parts by mass of the yellow reduced pyrroloquinoline quinone crystal. A content of ethanol of 5 parts by mass or more tends to enhance antibacterial properties more significantly. A content of ethanol of 200 parts by mass or less tends to enhance stability more significantly.

(Other Additives)

The composition may further contain other additives. Examples of the other additives include, but are not particularly limited to, emulsifying agents, tensing agents, buffers, dissolution aids, corrigents, antiseptics, stabilizing agents, and antioxidants.

[Method of Producing Composition]

The method of producing a composition according to the present embodiment comprises a step of removing ethanol and/or water from a solution containing the yellow reduced pyrroloquinoline quinone crystal, cyclodextrin, and ethanol and/or water. If a solution containing the yellow reduced pyrroloquinoline quinone crystal, cyclodextrin, and ethanol and/or water is prepared and mixed with a wet process, a clathrate cyclodextrin can readily trap the yellow reduced pyrroloquinoline quinone crystal.

Examples of the method of preparing the solution include, but are not particularly limited to, a method of mixing components, and stirring the components for 2 minutes to several hours. The solution may be in the form of a paste by adjusting the amount(s) of ethanol and/or water used.

Examples of the method of removing ethanol and/or water from the solution include, but are not particularly limited to, typical drying methods such as drying under reduced pressure, spray drying, and freeze drying.

The composition obtained as above can prevent generation of precipitates and can be stably stored in low temperature storage, room temperature storage, anaerobic storage in air tight containers, and storage by blocking light.

[Gel]

The gel according to the present embodiment contains the yellow reduced pyrroloquinoline quinone crystal and ethanol. The yellow reduced pyrroloquinoline quinone crystal can be gelled without using any gelling agent, and can attain a gel having high dispersibility. For this reason, the gel according to the present embodiment can be suitably used in applications to gelled products.

Figure 6:
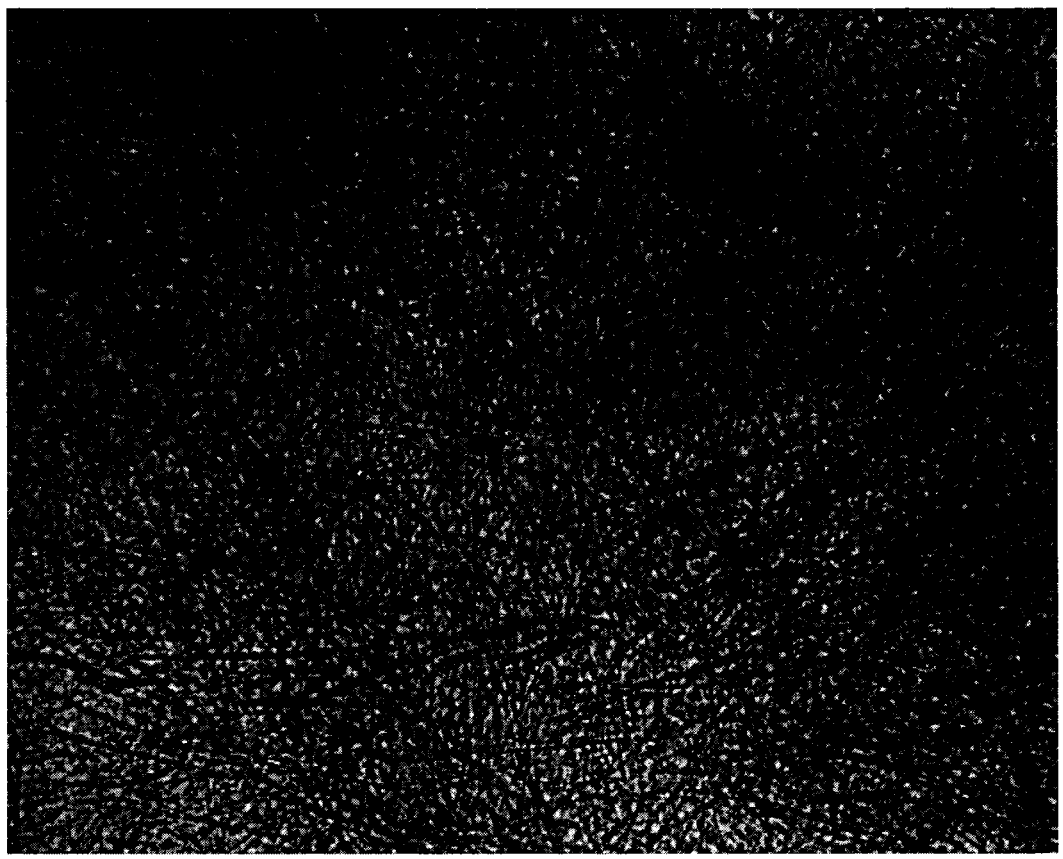
FIG. 6 shows a drawing showing an optical microscopic photograph (magnification: 40 times) of an orange gelled product obtained in Example 7.

FIG. 6 shows the result of observation of an orange gelled product obtained in Example 7 described later with an optical microscope (magnification: 40 times). As shown in FIG. 6, fibrous substances are generated in the gelled product, and presumably these fibrous substances support the solvent to generate the gelled product. It seems that one non-limiting reason is that the crystal structure of the yellow reduced pyrroloquinoline quinone crystal is readily changeable and changes into fibers in a concentration exceeding the solubility of the solvent. It seems that one non-limiting reason why a low molecular compound such as PQQ forms such a fiber structure is that low molecular compounds are bonded to each other into a polymer through a weak interaction such as a hydrogen bond or π-π interaction.

[Method of Producing Gel]

Examples of the method of producing a gel include, but are not particularly limited to, a method of mixing the yellow reduced pyrroloquinoline quinone crystal with ethanol, and stirring or ultrasonically treating the mixture to provide a gel.

[Applications]

The yellow reduced pyrroloquinoline quinone crystal according to the present embodiment, and the composition and the gel containing the crystal can be used as an effective component for products for humans or animals, such as foods, feedstuffs, pharmaceuticals, quasi-drugs, and cosmetics.

[Foods]

The foods according to the present embodiment contain the yellow reduced pyrroloquinoline quinone crystal or the gel. Examples of the foods include, but are not particularly limited to, daily foods and beverages, a variety of hospital diets, functional foods, and feedstuffs. The functional foods here refer to foods to be taken for maintaining health or for nutritional support instead of meals, such as health foods, dietary supplements, foods with nutrient function claims, and foods for specified health uses. Examples of the specific form thereof include, but are not limited to, capsules, tablets, chewables, tablets, and drinks.

If the yellow reduced pyrroloquinoline quinone crystal according to the present embodiment is made into a functional food, the following additives used for foods can be used, for example: sweeteners, coloring agents, preservatives, thickening stabilizers, antioxidants, color fixatives, bleaching agents, antibacterial and antifungal agents, gum bases, bittering agents, enzymes, glossing agents, acidulants, seasonings, emulsifying agents, strengthening agents, production agents, fragrances, and spice extracts. Usually, these additives can also be added to daily foods, such as miso, soy source, freeze-dried miso soup, ramen, fried noodle, curry, corn soup, mapo tofu, mapo eggplant, pasta sources, pudding, cake, and bread.

Water and an organic solvent may be contained in applications to foods. Examples of the organic solvent used in foods include, but are not particularly limited to, oils and fats, and alcohols. The yellow reduced pyrroloquinoline quinone crystal according to the present embodiment has high solubility in alcohols, and can be supplied in the form of a tincture.

Examples of the alcohols include, but are not particularly limited to, methanol, ethanol, propanol, butanol, glycerol, propylene glycol, and ethylene glycol. Among these alcohols, preferred is ethanol, which has particularly high solubility and can be used for edible purposes. Water is also preferred from the same viewpoint.

[Pharmaceuticals]

The pharmaceuticals or the quasi-drugs according to the present embodiment contain the yellow reduced pyrroloquinoline quinone crystal. Examples of the pharmaceuticals or the quasi-drugs include, but are not particularly limited to, external preparations for skin, injections, oral preparations, and suppositories.

Examples of administration modes of the pharmaceuticals or the quasi-drugs to be used include, but are not particularly limited to, oral administrations or parenteral administrations such as intravenous, endoperitoneal, subdermal, or dermal administration. Examples of the form thereof include, but are not particularly limited to, tablets, powders, granules, pills, suspensions, emulsions, infusions and decoctions, capsules, syrups, liquids, elixirs, extracts, tinctures, fluid extracts, injections, drops, creams, and suppositories.

In particular, the form of a tablet may be composed of the yellow reduced pyrroloquinoline quinone crystal alone or composed of a mixture of the yellow reduced pyrroloquinoline quinone crystal and various additives and the like. Preferably, various excipients, lubricants and the like are added to the yellow reduced pyrroloquinoline quinone crystal, and the mixture is tableted into tablets. As the method of producing tableted products, for example, direct compression molding method can be used. Specifically, examples of such the method include a method of mixing powdery components as homogeneously as possible, and directly feeding the mixture to a tableting machine to form the mixture into tablets. Examples of the tableting machine include, but are not particularly limited to, tableting machines such as a rotary tableting machine Correct 12HU (manufactured by Kikusui Seisakusho Ltd.). These tableting machines can mold the mixture at low pressure. For example, the tableting can be performed at a pressure of about 1 to 3 t.

The tablet hardness of the tableted product thus obtained is 3 to 20 kgf, preferably 5 to 15 kgf. A tablet hardness of more than 3 kgf is preferable because the resulting tableted product is unlikely to be broken on the production line or during distribution. A tablet hardness of less than 20 kgf is preferable because the resulting tableted product is not too hard and has a preferable texture such that the contents are unlikely to be eluted, and thus the absorption rate tends to be suitable.

The size of the tableted product thus obtained is not particularly limited, and is preferably appropriately selected according to the amount of PQQ to be administrated, the amount of other ingredients to be added, or the number of times of administration. For example, because of administration, a tablet preferably has a diameter of generally 5 to 20 mm, and preferably has a weight of 200 to 2000 mg. The tableted product can have any shape such as round, rectangular, hexagonal, cylindrical, or round biconvex shapes without particular limitation.

In formulation of oral preparations, the following additives can be used without particular limitation, for example: excipients, binders, disintegrants, lubricants, dispersing agents, suspending agents, emulsifying agents, diluents, buffers, antioxidants, and microbial inhibitors.

The yellow reduced pyrroloquinoline quinone crystal according to the present embodiment and the composition containing the yellow reduced pyrroloquinoline quinone crystal can be formulated in the form of a liquid formulation suitable for oral administration such as a syrup by addition of water; saccharides such as fructose, sucrose, sorbitol, and glucose; oils such as peanut oil, soybean oil, olive oil, and sesame oil; glycols such as polyethylene glycol and polypropylene glycol; antiseptics such as p-hydroxybenzoic acid esters; para-oxybenzoic acid derivatives such as methyl para-oxybenzoate; preservatives such as sodium benzoate; and flavors such as strawberry flavor and peppermint flavor.

The yellow reduced pyrroloquinoline quinone crystal according to the present embodiment and the composition containing the yellow reduced pyrroloquinoline quinone crystal can be formulated in the form of formulations suitable for oral administration, such as tablets, capsules, powders, granules, powders, or granules by addition of a variety of additives. Examples of the additives include, but are not particularly limited to, saccharides such as lactose, sucrose, glucose, mannitol, and sorbitol; starches such as potato, wheat, and corn; inorganic substances such as calcium carbonate, calcium sulfate, sodium hydrogen carbonate, and sodium chloride; excipients composed of plant powders or the like such as crystalline cellulose, liquorice powder, and gentian powder; lubricants such as kaolin, talc, magnesium stearate, hydrogenating vegetable oil, macrogol, and silicone oil; disintegrants such as starch, sodium alginate, agar, gelatin powder, crystalline cellulose, carmellose sodium, carmellose calcium, calcium carbonate, and sodium hydrogen carbonate; binders such as poly(vinyl alcohol), cellulose, gelatin, hydroxypropyl cellulose, methyl cellulose, ethyl cellulose, carmellose, and starch glue solutions; surfactants such as fatty acid esters; and plasticizers such as glycerol. Dissolution enhancers, fillers and the like may be added when necessary.

The yellow reduced pyrroloquinoline quinone crystal according to the present embodiment and the composition containing the yellow reduced pyrroloquinoline quinone crystal in the form of formulations for oral administration may contain additives generally used in foods and beverages, such as food sweeteners, coloring agents, preservatives, thickening stabilizers, antioxidants, color fixatives, bleaching agents, fungicides, gum bases, bittering agents, enzymes, glossing agents, acidulants, seasonings, emulsifying agents, strengthening agents, production agents, fragrances, and spice extraction. The formulations suitable for oral administration can be used as they are, can be used in the form of powder foods, sheet foods, jarred foods, canned foods, retort foods, capsulated foods, tableted foods, fluid foods, and drinks, or can be used as foods and beverages such as health foods, functional foods, and dietary supplements.

Furthermore, the yellow reduced pyrroloquinoline quinone crystal according to the present embodiment can be used in combination with, for example, vitamins such as vitamins B, vitamin C, and vitamin E; amino acids; carotenoids such as astaxanthin, α-carotene, and β-carotene; ω-3 fatty acids such as docosahexaenoic acid and eicosapentaenoic acid; and ω-6 fatty acids such as arachidonic acid when necessary.

EXAMPLES

The present embodiment will now be described in more detail by way of Examples and Comparative Examples, but the present embodiment is not limited to these Examples.
[Reagent]
Pyrroloquinoline quinone disodium: manufactured by Mitsubishi Gas Chemical Company, Inc. (trade name: BioPQQ)
L-ascorbic acid: manufactured by Wako Pure Chemical Industries, Ltd.
[Measurement by Powder X-Ray Diffraction]
The crystals obtained in Examples and Comparative Examples were extracted, and were analyzed with a single-crystal X-ray structure analyzer according to single-crystal X-ray structure analysis by powder X-ray diffraction on the following conditions:

(Measurement Conditions)
apparatus: RINT2500 manufactured by RIGAKU Corp.
X rays: Cu-Kα/tube voltage: 40 kV/tube current: 100 mA
scanning speed: 4.000°/min
sampling width: 0.020°

Example 1

Pyrroloquinoline quinone disodium (3.0 g) was dissolved in water (1.2 L) to obtain Solution A. L-ascorbic acid (30 g), water (120 g), and 2N hydrochloric acid (2.5 g) were mixed, and the temperature was controlled to 12° C. to obtain Solution B. Solution A was added to Solution B over two hours under stirring to obtain a mixed solution. At this time, the pH of the mixed solution was 2.96. The mixed solution was then stirred at 20° C. for 18 hours. The resulting solution was mixed with 2N hydrochloric acid (2.5 g), and was further stirred for one hour. The crystals precipitated in the mixed solution were filtered through a Buchner funnel, and were washed with 2N hydrochloric acid (5 mL) and an aqueous solution of 50% ethanol (8 mL). The resulting crystals were then dried at room temperature under reduced pressure for 20 hours to obtain a yellow ocher hydrated crystal (3.35 g).

The result of powder X-ray diffraction measurement of the resulting crystal is shown in FIG. 1. This crystal had 2θ peaks at 7.05°, 10.66°, 11.19°, 16.35°, 23.75°, and 25.55°.

Comparative Example 1 Experiment Based on WO2011/102387

Solution A was added to Solution B in the same manner as in Example 1, and was stirred at 70° C. for two hours. After the stirring, crystals were precipitated in the mixed solution. Hydrochloric acid was added to the mixed solution to adjust the pH to 1 or less. The crystals precipitated in the mixed solution were filtered through a Buchner funnel, and were washed with 2N hydrochloric acid (5 mL) and an aqueous solution of 50% ethanol (8 mL). The resulting crystals were then dried at 70° C. under reduced pressure for 18 hours to obtain a black solid (2.6 g).

Figure 2:
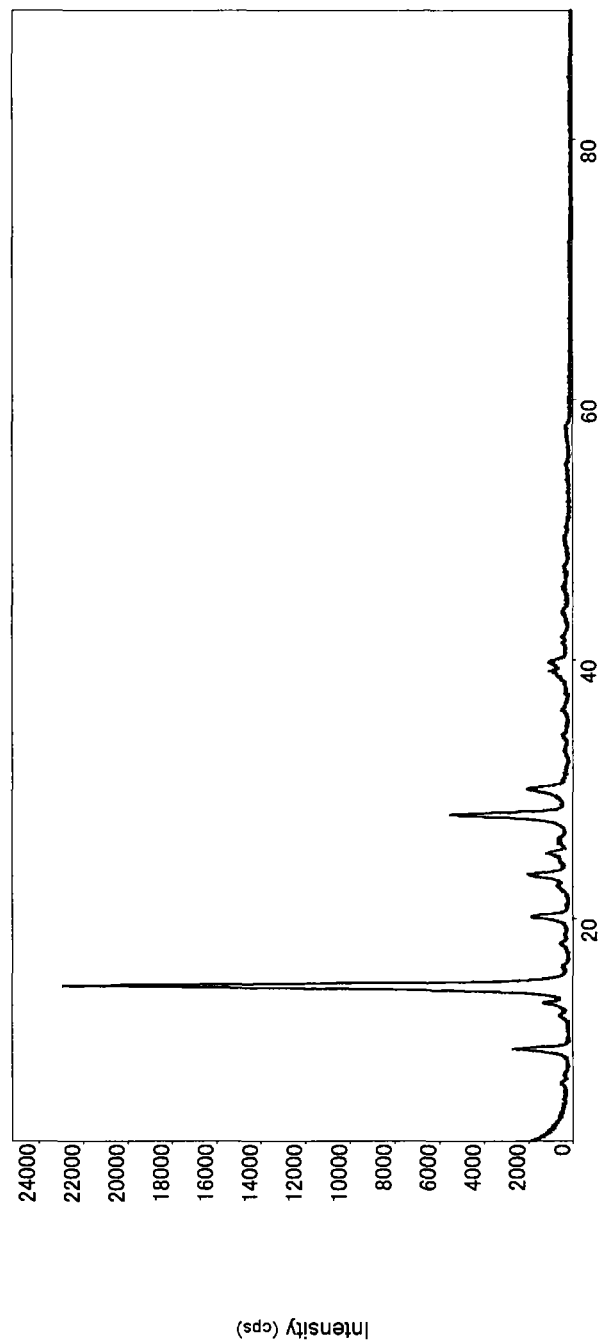
FIG. 2 shows a drawing showing the result of powder X-ray diffraction of a black reduced pyrroloquinoline quinone crystal in Comparative Example 1.

The result of powder X-ray diffraction measurement of the resulting solid is shown in FIG. 2. This solid was a crystal having 2θ peaks at 10.11°, 13.62°, 14.92°, and 28.04°.

Example 2

The crystals obtained by the same operation as that in Example 1 were dried at 70° C. under reduced pressure for 20 hours. The crystals changed into the slightly greenish yellow crystals.

Figure 3:
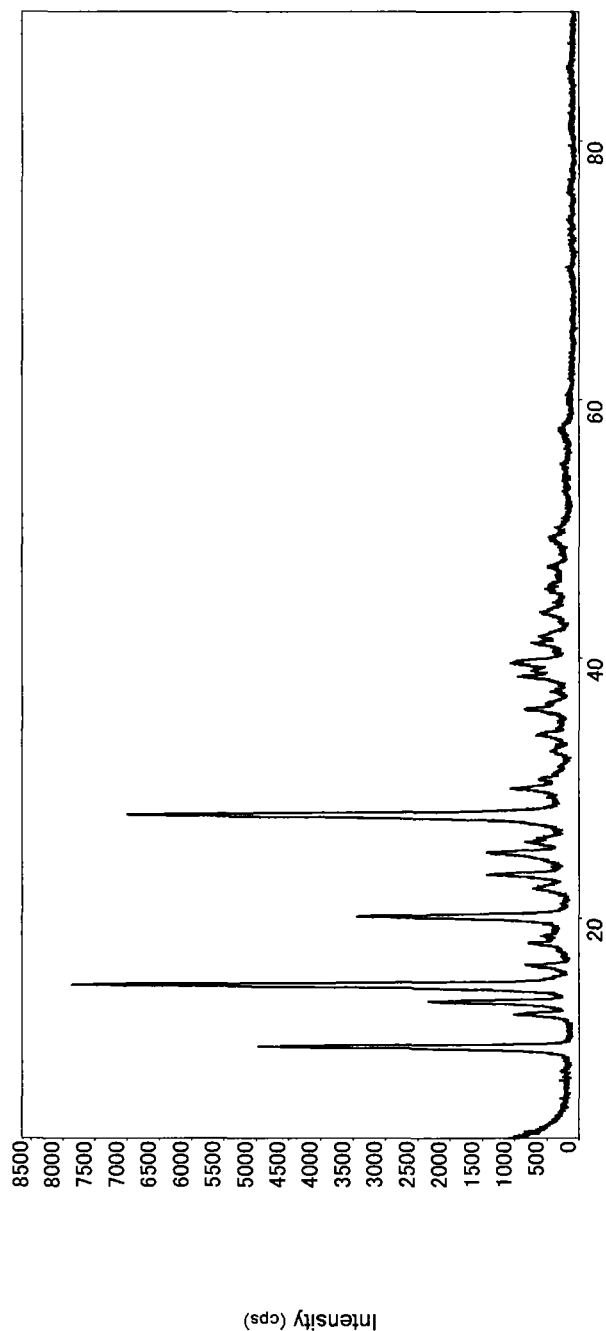
FIG. 3 shows a drawing showing the result of powder X-ray diffraction of a yellow ocher reduced pyrroloquinoline quinone crystal in Example 2.

The result of powder X-ray diffraction measurement of the resulting crystal is shown in FIG. 3. This crystal had 2θ peaks at 6.85°, 10.49°, 11.02°, 16.18°, 23.57°, and 25.36°.

Example 3 Stirring Crystallization

Pyrroloquinoline quinone disodium (3.0 g) was dissolved in water (1.2 L) to obtain Solution A. L-ascorbic acid (30 g) and water (120 g) were mixed, and the temperature was controlled to 18° C. to obtain Solution B. Solution A was added to Solution B over two hours under stirring to obtain a mixed solution. At this time, the pH of the mixed solution was 3.1. The mixed solution was then stirred at 20° C. for 18 hours. The crystals precipitated in the mixed solution were filtered through a Buchner funnel, and were washed with an aqueous solution of 50% ethanol (8 mL). The resulting crystals were then dried at room temperature under reduced pressure for 20 hours to obtain a yellow ocher hydrated crystal (3.87 g).

Figure 4:
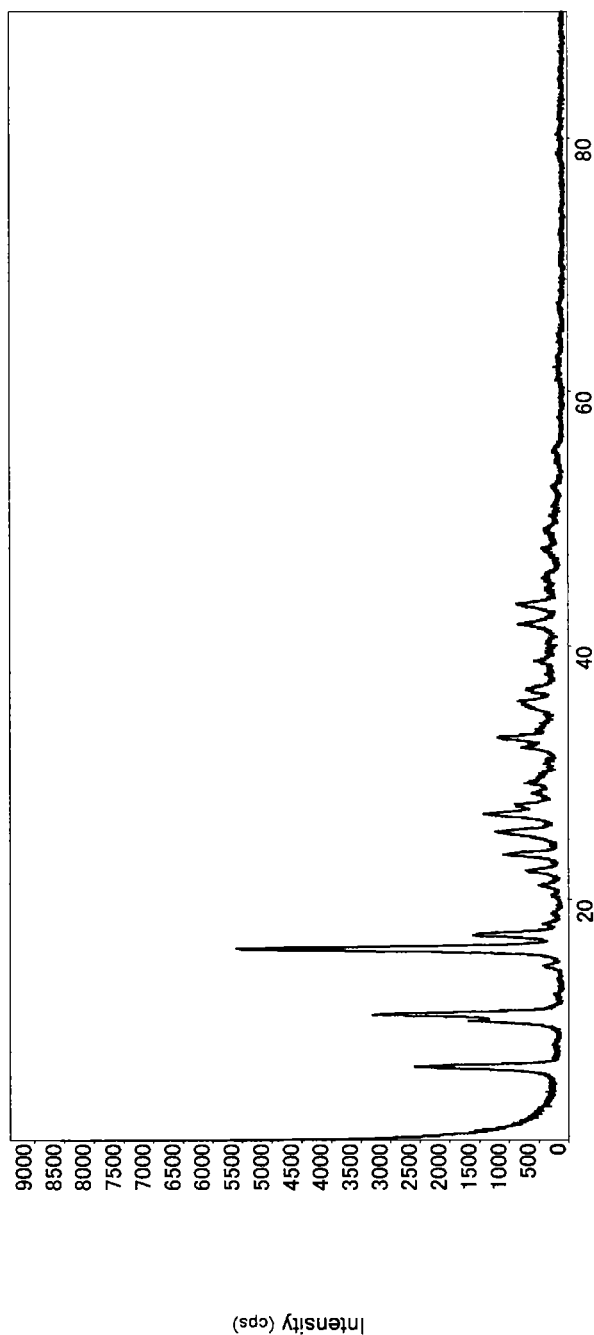
FIG. 4 shows a drawing showing the result of powder X-ray diffraction of a yellow ocher reduced pyrroloquinoline quinone crystal in Example 3.

The result of powder X-ray diffraction measurement of the resulting crystal is shown in FIG. 4. This crystal had 2θ peaks at 6.75°, 10.35°, 10.90°, 16.03°, 23.42°, and 25.24°.

Comparative Example 2 Dimethyl Sulfoxide-Acetonitrile Recrystallization

Recrystallization was performed on the conditions described in Bull. Chem. Soc. Jpn, 59, 1911-1914 (1986). The crystal (1 g) obtained in Example was dissolved in dimethyl sulfoxide (7 g), and acetonitrile (200 mL) was added. Yellow crystals were then precipitated. These yellow crystals were filtered, and were then dried under reduced pressure to obtain a yellow ocher solid (0.85 g).

Figure 5:
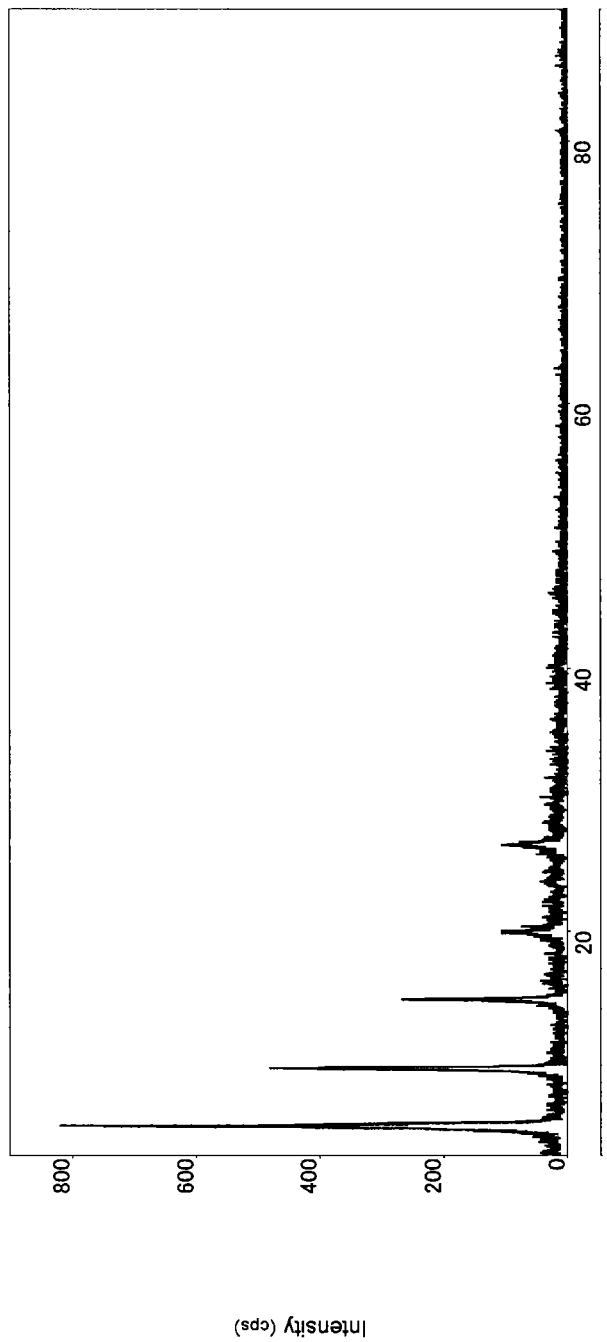
FIG. 5 shows a drawing showing the result of powder X-ray diffraction of a reduced pyrroloquinoline quinone crystal in Comparative Example 2.

The result of powder X-ray diffraction measurement of the solid is shown in FIG. 5. This solid was a substance having 2θ peaks at 5.21°, 9.62°, 14.84°, 19.97°, and 26.52°. The result shows that the resulting crystal was different from the crystals obtained in Examples, and had a small peak intensity and low crystallinity. The solid might have a residual organic solvent (acetonitrile), and was not suitable in applications to foods, beverages and the like.

Comparative Example 3

The same operation as in Example 1 was performed except that the mixed solution was left to stand at 20° C. for 18 hours, to obtain a gelled red black solid (3.35 g).

Comparative Example 4

The same operation as in Example 1 was performed except that the mixed solution was left to stand at 20° C. for 72 hours, to obtain a black solid (3.2 g).

Comparative Example 5

The same operation as in Example 1 was performed except that the mixed solution was stirred at 25° C. for 18 hours, to obtain a black solid (2.9 g).

Comparative Example 6

The same operation as in Example 1 was performed except that the mixed solution was left to stand at 25° C. for 18 hours, to obtain a gelled red black solid (3.0 g).

Comparative Example 7

The same operation as in Example 1 was performed except that the mixed solution was stirred at 30° C. for 18 hours, to obtain a red brown solid (3.0 g).

Comparative Example 8

The same operation as in Example 1 was performed except that the mixed solution was left to stand at 30° C. for 18 hours, to obtain a red brown solid (3.0 g).
[Measurement by NMR]

The crystals obtained in Example 1, Example 3, and Comparative Example 1 were measured at room temperature with a 500 MHz NMR, JNM-ECA500 spectrometer manufactured by JEOL, Ltd. to obtain the $^{13}$C-NMR spectrums.

The results show that all of the crystals had peaks at 105.7, 111.0, 119.4, 122.9, 123.6, 128.1, 131.3, 134.2, 137.8, 140.9, 142.6, 162.2, 165.5, and 170.1 ppm (reference: dimethyl sulfoxide-$d_6$: 39.5 ppm).

The obtained spectrums corresponded to the $^{13}$C-NMR spectrum of the reductant described in Non Patent Literature 3, and it was confirmed that the same reductants were generated in Example 1, Example 3, and Comparative Example 1. The obtained spectrums had no peaks at 173.3 and 178.0 ppm, which are derived from the quinone structure, in the measurement data.
[Counter Metal Ion Analysis on Reduced PQQ]

Each of the crystals obtained in Example 1, Example 3, and Comparative Example 1 was dissolved in a choline hydroxide aqueous solution. The Na ion concentration in each solution was analyzed with a sodium ion electrode manufactured by HORIBA, Ltd. The results show that the sodium content of each solution was 1/300 or less of that of the solution of pyrroloquinoline quinone disodium used as the raw material. It indicates that the resulting crystals contained a considerable amount of reduced pyrroloquinoline quinone in the free form.
[Test on Solubility in Ethanol]

Example 4

The crystal (40 mg) obtained in Example 1 was added to ethanol (2 mL), and was ultrasonically treated for one minute. The solution was left at room temperature for 30 minutes or more, and thereafter the resulting precipitate was centrifuged and the resulting supernatant was diluted with dimethyl sulfoxide to analyze the concentration at an absorbance at 330 nm. The concentration was 8.5 mg/mL, indicating that the crystal had excellent solubility.

Example 5

The crystal (40 mg) obtained in Example 2 was added to ethanol (2 mL), and was ultrasonically treated for one minute. The solution was left at room temperature for 30 minutes or more, and thereafter the resulting precipitate was centrifuged and the resulting supernatant was diluted with dimethyl sulfoxide to analyze the concentration at an absorbance at 330 nm. The concentration was 3.2 mg/ML, indicating the crystal had excellent solubility.

Comparative Example 9

The crystal (40 mg) obtained in Comparative Example 1 was added to ethanol (2 mL), and was ultrasonically treated for one minute. The solution was left at room temperature for 30 minutes or more, and thereafter the resulting precipitate was centrifuged and the resulting supernatant was diluted with dimethyl sulfoxide to analyze the concentration at an absorbance at 330 nm. The concentration was 1.4 mg/ML. The results show that the crystals obtained in Examples 1 and 2 had quite excellent solubility.
[Dispersibility in Ethanol: Gelation Test]

Example 6

The crystal (20 mg) obtained in Example 1 was added to ethanol (2 mL), and was ultrasonically treated for one minute. The solution was left at 20° C. for two hours, and then turned into an orange gelled product. After the solution was left for three hours, the solution was homogenous without any difference between upper and lower portions of the solution. The gelled product was generated through the following process: the reduced PQQ crystals according to the present invention turned into fibers, and alcohol was encapsulated between these fibers in the form of a net to generate a gel. This gelled product (20 μL) was added to water (1 mL) to generate a yellow homogenous dispersion.

The resulting orange gelled product was observed with an optical microscope (magnification: 40 times). The result is shown in FIG. 6. The microscopic photograph shows a fibrous substance, which supported the solvent to generate a gelled product.

Comparative Example 10

The solid (20 mg) obtained in Comparative Example 1 was added to ethanol (2 mL), and was ultrasonically treated for one minute. The solution was left at 20° C. for two hours, a black solid was sedimented and the solution was slightly yellowed. The solution had a difference between the upper and lower portions, and was required to be controlled while being stirred to feed a solution having a homogeneous concentration. This ethanol mixture (20 μL) was added to water (1 mL) to generate a solution having a black solid sedimented therein. The result shows that the crystal obtained in Example 1 had significantly high dispersibility.

[Test on Solubility in Water]

Example 7

The crystal (30 mg) obtained in Example 1 was added to water (1 mL), and was ultrasonically treated for one minute. The solution was left at room temperature for 30 minutes or more, and thereafter the resulting precipitate was centrifuged and the resulting supernatant was diluted with water to analyze the concentration at an absorbance at 310 nm. The concentration was 0.13 mg/mL.

Example 8

The crystal (30 mg) obtained in Example 2 was added to water (1 mL), and was ultrasonically treated for one minute. The solution was left at room temperature for 30 minutes or more, and thereafter the resulting precipitate was centrifuged and the resulting supernatant was diluted with water to analyze the concentration at an absorbance at 310 nm. The concentration was 0.14 mg/mL.

Comparative Example 11

The solid (30 mg) obtained in Comparative Example 1 was added to water (1 mL), and was ultrasonically treated for one minute. The solution was left at room temperature for 30 minutes or more, and thereafter the resulting precipitate was centrifuged and the resulting supernatant was diluted with water to analyze the concentration at an absorbance at 310 nm. The concentration was 0.019 mg/mL. The result shows that the crystals obtained in Examples 1 and 2 had excellent solubility.

[Test on Stability of Crystal (Dispersed in Water)]

Example 9

The crystal (0.2 g) obtained in Example 1 was mixed with water (1 mL). The solution was left at room temperature for one hour to generate a yellow homogenous dispersion. After the yellow homogenous dispersion was left at room temperature for two days, the dispersion remained the same.

Comparative Example 12

The solid (0.2 g) obtained in Comparative Example 1 was mixed with water (1 mL). The solution was left at room temperature for one hour to generate a solution having a black solid sedimented therein.

Comparative Example 13

The crystal (0.2 g) obtained in Comparative Example 2 was mixed with water (1 mL). The solution was left at room temperature for one hour to generate a dark red dispersion. After the dispersion was left at room temperature for two days, a black precipitate was generated and the solution was not homogenous.

The results show that the crystal according to the present invention remained yellow. The results also show that the crystal according to the present invention had excellent dispersibility.

[Method of Producing Composition]

[Example 10] Composition Containing 10% Yellow Reduced Pyrroloquinoline Quinone Crystal (Using Water)

The yellow ocher hydrated crystal (0.1 g) obtained in Example 1, γ-cyclodextrin (0.9 g), and water (50 g) were mixed. The solution was then dried under reduced pressure with an evaporator to remove water from the resulting solution to obtain a red composition (1 g). The bath temperature was 40° C., and the final pressure was 12 mbar.

[Example 11] Composition Containing 10% Yellow Reduced Pyrroloquinoline Quinone Crystal (Using Ethanol Aqueous Solution)

The yellow ocher hydrated crystal (0.1 g) obtained in Example 1, ethanol (70 g), γ-cyclodextrin (0.9 g), and water (20 g) were mixed. The solution was then dried under reduced pressure with an evaporator to remove water from the resulting solution to obtain a red composition (1 g). The bath temperature was 40° C., and the final pressure was 12 mbar.

[Example 12] Composition Containing 10% Yellow Reduced Pyrroloquinoline Quinone Crystal (Using Ethanol)

The yellow ocher hydrated crystal (0.1 g) obtained in Example 1, ethanol (80 g), and γ-cyclodextrin (0.9 g) were mixed. The solution was then dried under reduced pressure with an evaporator to remove water from the resulting solution to obtain a brown composition (1 g). The bath temperature was 40° C., and the final pressure was 12 mbar.

[Example 13] Composition Containing 5% Yellow Reduced Pyrroloquinoline Quinone Crystal (Using Ethanol)

The yellow ocher hydrated crystal (0.05 g) obtained in Example 1, ethanol (80 g), and γ-cyclodextrin (0.95 g) were mixed. The solution was then dried under reduced pressure with an evaporator to remove water from the resulting solution to obtain a brown composition (1 g). The bath temperature was 40° C., and the final pressure was 12 mbar.

[Example 14] Composition Containing Saturated Yellow Reduced Pyrroloquinoline Quinone Crystal (Using Water)

The yellow ocher hydrated crystal (30 mg) obtained in Example 1 was added to an aqueous solution (1 mL) of 20% cyclodextrin, and was ultrasonically treated for two minutes. The resulting solution was centrifuged to remove undissolved solid contents to obtain a composition containing saturated yellow reduced pyrroloquinoline quinone crystal.

[Comparative Example 14] Aqueous Solution Containing Saturated Yellow Reduced Pyrroloquinoline Quinone Crystal The yellow ocher hydrated crystal (30 mg) obtained in Example 1 was added to water (1 mL), and was ultrasonically treated for two minutes. The resulting solution was centrifuged to remove undissolved solid contents to obtain an aqueous solution containing saturated yellow reduced pyrroloquinoline quinone crystal.

[Measurement of Saturated Solubility]

The compositions (30 mg) obtained in Examples 11, 13, and 14 and Comparative Example 14 each were added to water (1 mL), and were ultrasonically treated for two minutes. The resulting solutions were then centrifuged. The supernatants were diluted with water, and were subjected to UV measurement. The results are shown in Table 1 below.

TABLE 1

|  | Solubility (μg/ML) |
| --- | --- |
| Example 11 | 975 |
| Example 13 | 965 |
| Example 14 | 23800 |
| Comparative Example 14 | 130 |

[Evaluation on Stability]

The supernatant solutions obtained during the measurement of saturated solubility were left at room temperature for one day, and were observed. One day later, no precipitate was found in the aqueous solutions used in the above experiment.

The results of the measurement of saturated solubility and evaluation on stability show that the compositions according to the present invention have high stability and enhanced solubility of the yellow reduced pyrroloquinoline quinone crystal.

[Crystal Structure]

The compositions in Examples 10 and 12 and γ-cyclodextrin were subjected to powder X-ray diffraction measurement. The measurement by powder X-ray diffraction was performed on the following conditions:
  apparatus: RINT2500 manufactured by RIGAKU Corp.
  X rays: Cu-Kα/tube voltage: 40 kV/tube current: 100 mA
  scanning speed: 4.000°/min
  sampling width: 0.020°

Figure 7:
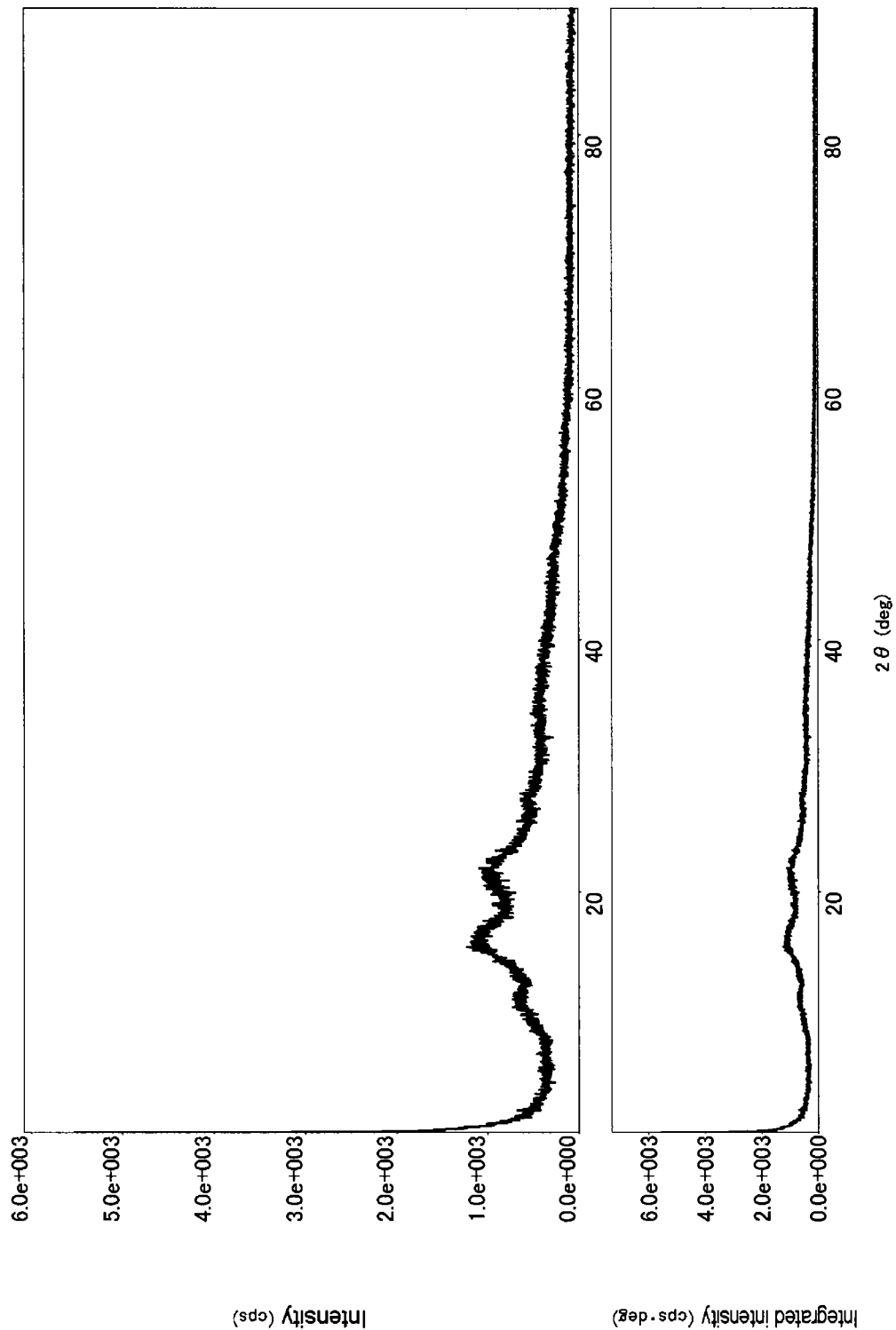
FIG. 7 shows a drawing showing the result of powder X-ray diffraction of the composition in Example 8.
Figure 8:
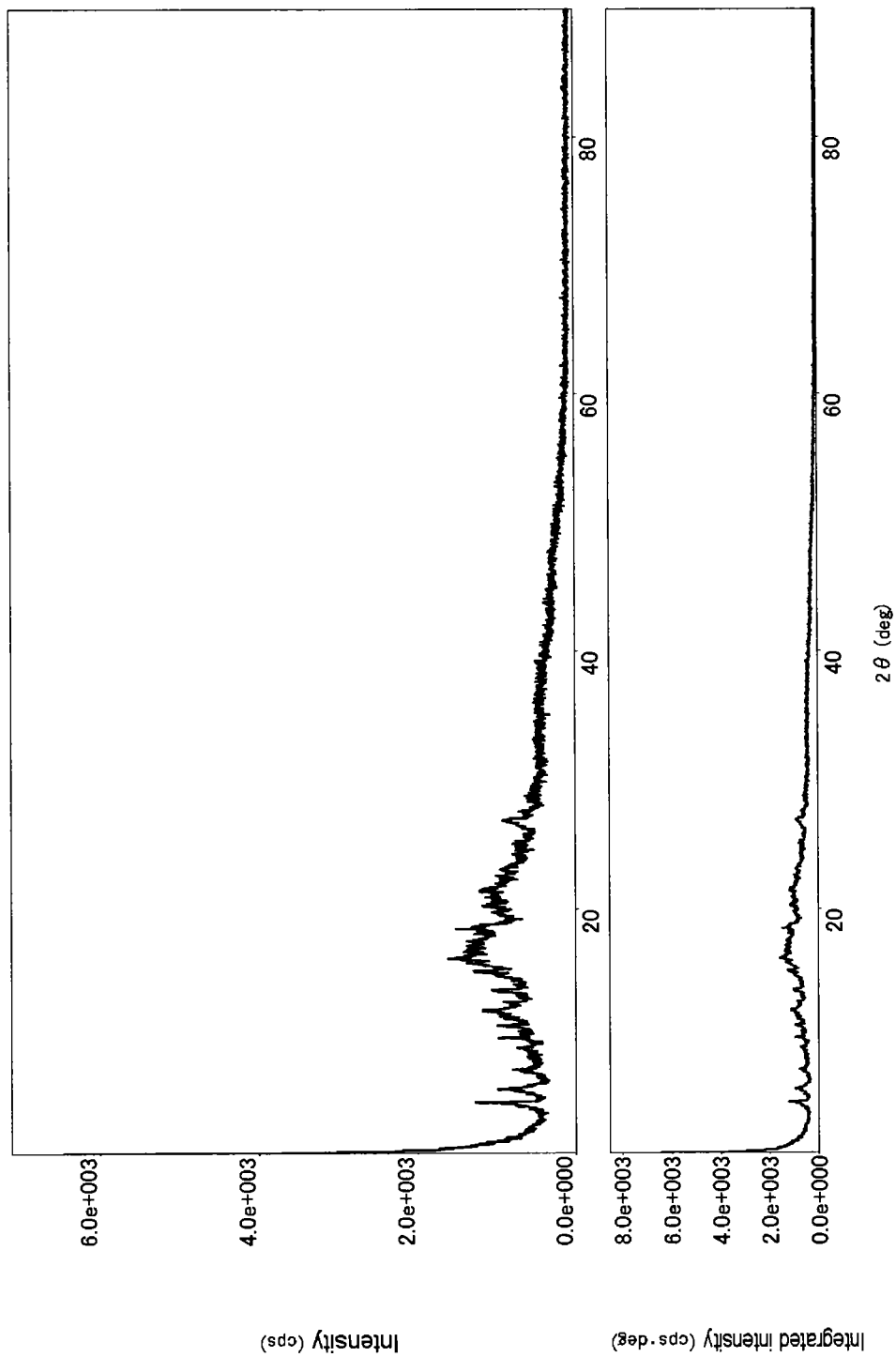
FIG. 8 shows a drawing showing the result of powder X-ray diffraction of the composition in Example 10.
Figure 9:
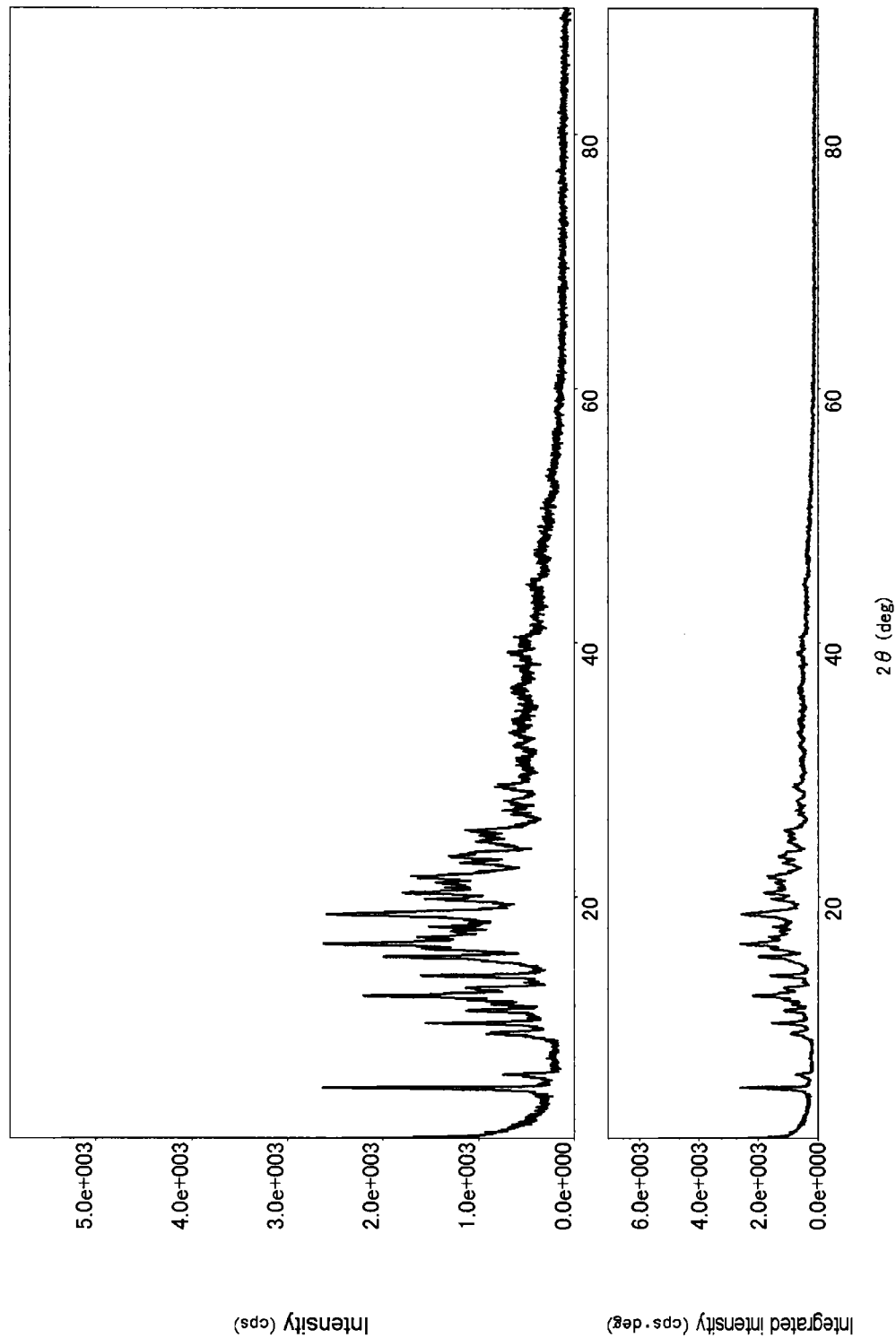
FIG. 9 shows a drawing showing the result of powder X-ray diffraction of γ-cyclodextrin.

The measurement results show that the composition in Example 10 had a broad distribution of peaks derived from cyclodextrin, which indicates that the composition was amorphous. The results confirms that the composition in Example 12 had a crystal structure of cyclodextrin. The measurement results are shown in FIGS. 7 to 9.

[Proton Nuclear Magnetic Resonance (NMR) Analysis]

The composition in Example 14 and the composition in Comparative Example 14 each were dissolved in deuterated water, and were subjected H-NMR measurement using trimethylsilyl propanoic acid as a reference.

The measurement results show that the composition in Example 14 had peaks at 7.19 and 8.36 ppm derived from the yellow reduced pyrroloquinoline quinone crystal and peaks at 3.4-4.7 (m), 5.36 ppm derived from cyclodextrin. The results show that the composition in Comparative Example 14 had peaks at 7.28 and 8.19 ppm derived from the yellow reduced pyrroloquinoline quinone crystal. It is conceivable that the two peak shifts derived from the yellow reduced pyrroloquinoline quinone crystal are obtained because the yellow reduced pyrroloquinoline quinone is trapped in a clathrate cyclodextrin.

This application is based on Japanese Patent Application No. 2013-093264, filed to the Japan Patent Office on Apr. 26, 2013, the contents of which are incorporated herein by reference.

INDUSTRIAL APPLICABILITY

The yellow reduced pyrroloquinoline quinone crystal according to the present invention has industrial applicability in the fields of medical drugs, functional foods, feedstuffs, cosmetics, and the like.

The invention claimed is:

1. A yellow reduced pyrroloquinoline quinone crystal having a solubility in water of 0.040 to 0.20 (mg/mL), wherein the yellow reduced pyrroloquinoline quinone crystal has 2θ peaks at 6.85±0.4°, 10.49±0.4°, 11.02±0.4°, 16.18±0.4°, 23.57±0.4°, and 25.36±0.4° in powder X-ray diffraction using Cu-Kα.

2. The yellow reduced pyrroloquinoline quinone crystal according to claim 1, wherein the yellow reduced pyrroloquinoline quinone crystal comprises reduced pyrroloquinoline quinone in a free form.

3. A food comprising the yellow reduced pyrroloquinoline quinone crystal according to claim 1.

4. A pharmaceutical comprising the yellow reduced pyrroloquinoline quinone crystal according to claim 1.

5. A gel comprising the yellow reduced pyrroloquinoline quinone crystal according to claim 1 and ethanol.

6. A food comprising the gel according to claim 5.

7. A composition comprising the yellow reduced pyrroloquinoline quinone crystal according to claim 1 and cyclodextrin.

8. The composition according to claim 7, wherein the cyclodextrin comprises γ-cyclodextrin.

9. The composition according to claim 7, wherein a content of the cyclodextrin is 1 to 2000 parts by mass based on 1 part by mass of the yellow reduced pyrroloquinoline quinone crystal.

10. The composition according to claim 7, further comprising water.

11. A method of producing a composition, comprising a step of removing ethanol and/or water from a solution containing the yellow reduced pyrroloquinoline quinone crystal according to claim 1, cyclodextrin, and the ethanol and/or the water.

12. A method of producing a yellow reduced pyrroloquinoline quinone crystal according to claim 1, comprising stirring a mixed solution containing pyrroloquinoline quinone and/or a salt of the pyrroloquinoline quinone and a reducing agent at a temperature of less than 25° C. for 10 hours or more.

13. The method of producing the yellow reduced pyrroloquinoline quinone crystal according to claim 12, wherein the reducing agent comprises ascorbic acid.

14. The method of producing the yellow reduced pyrroloquinoline quinone crystal according to claim 12, wherein the mixed solution has a pH of 1.5 to 3.5.

15. The method of producing the yellow reduced pyrroloquinoline quinone crystal according to claim 12, wherein a total content of the pyrroloquinoline quinone and the salt of the pyrroloquinoline quinone in the mixed solution is 0.0010 to 30 g/L.

16. The method of producing the yellow reduced pyrroloquinoline quinone crystal according to claim 12, wherein a content of the reducing agent in the mixed solution is 0.10 to 500 g/L.

17. The yellow reduced pyrroloquinoline quinone crystal according to claim 1, having a solubility in water of 0.060 to 0.18 (mg/mL).

18. The yellow reduced pyrroloquinoline quinone crystal according to claim 1, having a solubility in ethanol of 1.8 to 12.5 (mg/mL).

\* \* \* \* \*